United States Patent [19]

Hettche

[11] Patent Number: 5,164,194
[45] Date of Patent: Nov. 17, 1992

[54] AZELASTINE CONTAINING MEDICAMENTS

[75] Inventor: Helmut Hettche, Dietzenbach, Fed. Rep. of Germany

[73] Assignee: Asta Pharma AG, Fed. Rep. of Germany

[21] Appl. No.: 551,644

[22] Filed: Jul. 12, 1990

Related U.S. Application Data

[63] Continuation of Ser. No. 268,772, Nov. 9, 1988, abandoned.

[30] Foreign Application Priority Data

Nov. 13, 1987 [DE] Fed. Rep. of Germany ....... 3738681

[51] Int. Cl.⁵ .................. A61K 9/14; A61K 31/55
[52] U.S. Cl. .................... 424/489; 424/43; 424/45; 424/464; 424/422; 514/212
[58] Field of Search ............ 424/43, 464, 422, 45, 424/489; 514/212; 222/394; 141/24; 239/302; 248/108

[56] References Cited

U.S. PATENT DOCUMENTS

| 158,564 | 1/1875 | Barnes | 141/24 |
| 2,119,643 | 6/1938 | Mendl | 222/394 |
| 2,136,940 | 11/1938 | Ehbrecht | 222/394 |
| 2,457,024 | 12/1948 | Arp | 248/108 |
| 2,995,308 | 8/1961 | Ashkencz | 239/302 |
| 3,813,384 | 5/1974 | Vogelsang | 546/133 |
| 4,704,387 | 11/1987 | Engel et al. | 514/212 |
| 4,769,369 | 9/1988 | Thomas et al. | 514/234.5 |

FOREIGN PATENT DOCUMENTS

| 2164058 | 7/1972 | Fed. Rep. of Germany | 546/133 |
| 3530793 | 3/1986 | Fed. Rep. of Germany | 514/212 |
| 1377231 | 1/1972 | United Kingdom . | |

OTHER PUBLICATIONS

Negwer, Organic-Chemicals, Drugs and Their Synonyms, vol. II, (1987) p. 1145.
European Search Report.
Org.-Chem. drugs and their synonyms, vol. III, No. 6496 (1987).
Arzneimittel, Fortschritte 1972-1985, pp. 936 and 939 (1977).

Primary Examiner—Thurman K. Page
Assistant Examiner—Neil S. Levy
Attorney, Agent, or Firm—Cushman, Darby & Cushman

[57] ABSTRACT

A medicament for nasal use or for use in the eye which contains as active ingredient azelastine or a physiologically acceptable salt.

12 Claims, No Drawings

AZELASTINE CONTAINING MEDICAMENTS

This is a continuation of application Ser. No. 07/268,72, filed Nov. 9, 1988, now abandoned.

The present invention relates to the treatment of nasal and eye tissues with azelastine.

BACKGROUND OF THE INVENTION

Azelastine is a phthalazinone derivative having the following structural formula:

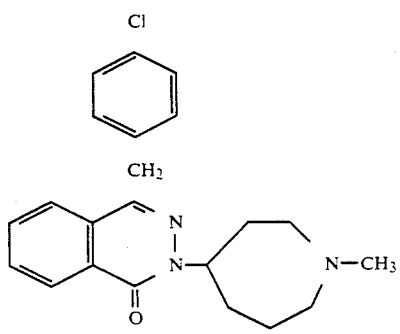

The chemical designation is: 4-(4-chlorobenzyl)-2-(perhydro-1-methyl-azepine-4-yl)-1-(2H)phthalazinone. Azelastine is used in particular for prophylactic treatment of asthma. Azelastine also has anti-allergic and antihistamine properties, see German Patent No. 21 64 058.

SUMMARY OF THE INVENTION

It has now been found that azelastine and its physiologically acceptable salts display particularly advantageous and surprising effects when the corresponding formulations are applied directly in the nose and/or to the conjunctival sac of the eye.

Elimination or marked relief has thus been achieved not only in allergy-related rhinitis, but also in the normal common cold (caused, for example, by rhino viruses) as well as in the vasomotor cold and the symptoms of illness triggered thereby.

It is surprising in this context that local nasal application also has a favorable effect on the mucous membrane of the eye (elimination or relief of reddening of the eye and of eye irritation) so that the additional use of eye drops is frequently superfluous.

Other indications for the application/use of the invention are, for example: non-specific conjunctivitis, allergy-related conjunctivitis, allergic blepharoedema, catarrhal conditions in the eye or nose, coryza.

Surprisingly, in addition, none of the tiredness that arises with other applications was observed with use according to the invention.

Furthermore the invention provides a way to overcome problems which arise because of azelastine's exceptionally penetrating, bitter taste. The degree of the bitter taste is so intense that it is even found to be unpleasant in a dilution of 1 : 706. This problem has hitherto prevented oral application of azelastine solutions, since patients refuse to take such azelastine solutions or suspensions. It wa surprisingly found in trial subjects that this bitter taste was no longer in evidence when the azelastine formulations of the invention were sprayed into the nose. As a result, it is possible in this manner to apply solutions or suspensions of azelastine and its salts nasally without taste impairment. Moreover the bitter taste is barely perceptible when the sprayed azelastine solution or suspension runs down into the pharynx.

Therefore, the object of the present invention is to provide a well tolerated and improved remedy based on azelastine or its salts for the treatment both of the allergy-related and vasomotor-related conditions as well as rhino virus-related cold and its accompanying symptoms.

A further object of the present invention is to provide medical formulations which are adapted to direct application to nasal and eye tissues.

The preferred embodiment of the invention is a sterile and stable aqueous solution of azelastine or one or more of its salts which can be used in the form of drops, ointments, creams, gels, insufflatable powders or, in a particularly preferred embodiment, in the form of a spray (preferably a nasal spray). The spray can be formed by the use of a conventional spray-squeeze bottle or a pump vaporizer. In addition, it is also possible to use compressed gas aerosols. For example 0.03 to 3 mg of azelastine base should be released per individual actuation.

Through the use of nasal drops or a nasal spray, the dosage of azelastine required for the treatment of the cold is lowered approximately tenfold and hence the incidence of the appearance of side effects is considerably lower than in the case of the application of azelastine in orally taken dosage forms such as tablets or syrups which distribute the active substance throughout the entire body. In the treatment of a banal illness such as a cold, a low incidence of side effects is particularly important and thus represents a considerable medical advance.

Solvents which may preferably be used for the formulations of the invention are: water, saturated aliphatic mono and polyvalent alcohols which contain 2-3 carbon atoms (for example ethanol, isopropanol, 1,2-propylene glycol, glycerine), liquid polyglycols (molecular weight 200 to 600).

The solvent used is preferably water or mixtures of water with other physiologically acceptable solvents (for example those mentioned above). Preferably, the amount of the latter solvent in the aqueous mixture should not exceed 15% by weight.

The solutions or formulations preferably contain preservatives and stabilizers. These include, for example: ethylene diamine tetra-acetic acid (edetic acid) and their alkali salts (for example dialkali salts such as disodium salt, calcium salt, calcium-sodium salt), lower alkyl p-hydroxybenzoates, chlorohexidine (for example in the form of the acetate or gluconate), phenyl mercury borate. Furthermore, it is possible, for example, to use sodium-(2- ethylmercurithio)-benzoate generally known as "thimerosal" which may be present in an amount of 0.001 to 0.05, preferably from 0.005 to 0.02, for example 0.01% (weight/volume in liquid formulations, otherwise weight/weight). Other suitable preservatives are: pharmaceutically useful quaternary ammonium compounds, for example cetylpyridinium chloride, tetradecyltrimethyl ammonium bromide, generally known as "cetrimide", benzyldimethyl-[2-[2-[p-(1,1,3,3-tetramethyl- butyl)]phenoxy]ethoxy]-ammonium chloride, generally known as "benzethonium chloride" and myristyl-:-picolinium chloride. Each of these compounds may be used in a concentration of 0.002 to 0.05, for example 0.02% (weight/volume in liquid formulations, otherwise weight/weight). Preferred preservatives among the quaternary ammonium compounds are, however, alkylbenzyl dimethyl ammonium chloride and mixtures thereof, for example the compounds generally known as "benzalkonium chloride". These latter consist of a mixture of the compounds of formula,

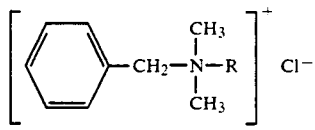

in which R represents an alkyl group having the formula $C_nH_{2n+1}$, wherein n represents a whole number from 8 to 18. The use of a mixture of compounds in which n represents 10 to 14 is particularly preferred and in particular the special compound in which $R=C_{12}H_{25}$ "Benzalkonium chloride" and the compounds of the above formula can be used in concentrations of 0.005 to 0.10, preferably of 0.005 to 0.05, for example of 0.01% (weight/volume for liquid formulations, otherwise weight/weight) and they may optionally be used in combination with 0.2 to 2.0, for example 0.4% (weight/ volume) of 2-phenylethanol.

The formulations of the invention (solutions, suspensions as well as oily solutions or suspensions, ointments, emulsions, creams, gels, dosage aerosols) contain 0.0005 to 2, preferably 0.001 to 1, in particular 0.003 to 0.5% (weight/weight) of azelastine (related to the free azelastine base). Should the azelastine be present-as a salt, the amounts should be recalculated as necessary to give the amounts of azelastine itself mentioned above. In the case of the eye drops, the same azelastine concentrations apply as in the case of the nasal forms.

In the case of powders, the concentration of azelastine base is 0.0005 to 2 percent by weight related to the solid carrier substances.

In the case of solutions, the dosage per nostril is, for example, 0.01 to 0.2 ml, in particular 0.05 to 0.15 ml. Such a dosage should be applied once to several times, preferably 1 to 5 times daily (optionally also hourly).

In the case of use at the eye (eye drops) the dosage is for example 1 drop (about 0.05 ml) of the solution or corresponding amounts of the semi-solid formulation forms.

Possible acid components for azelastine salts are, for example: hydrohalic acids (HCl, HBr), sulphuric acid, phosphoric acids ($H_3PO_4$, metaphosphoric acid, polyphosphoric acids), nitric acid, organic mono-, di- or tricarboxylic acids of aliphatic, alicyclic, aromatic or heterocyclic organic acids (embonic acid, citric acid, tartaric acid), aliphatic and aromatic sulfonic acids (for example camphorsulfonic acid).

The total amounts of preservatives in the formulations (solutions, ointments, etc.) is between 0.001 to 0.10, preferably 0.01 g per 100 ml of solution/suspension or 100 g of formulation.

In the case of preservatives, the following amounts of individual substances can, for example, be used:
thimero sal 0.002-0.02%;
benzalkonium chlorie 0.002 to 0.02% (in combination with thimero sal the amount of thimero sal is, for example =0.002 to 0.005%;);
chlorhexidine acetate or gluconate 0.01 to 0.02%;
phenyl mercuric/nitrate, borate, acetate 0.002-0.004%;
p-hydroxybenzoic acid ester (for example a mixture of the methyl ester and propyl ester 7 : 3): 0.05-0.15, preferably 0.1%.

The preservative used is preferably a combination of edetic acid (for example as the disodium salt) and benzalkonium chloride. In this combination, the edetic acid is used in a concentration of 0.05 to 0.1%, benzalkonium chloride being used in a concentration of 0.005 to 0.05%, preferably 0.01%.

In the case of solutions/suspensions reference is always made to percent by weight/volume, in the case of solid or semi-solid formulations to percent by weight/-weight of the formulation.

Further auxiliary substances which may, for example, be used for the formulations of the invention are: polyvinyl pyrrolidone, sorbitan fatty acid esters such as sorbitan trioleate, polyethoxylated sorbitan fatty acid esters (for example polyethoxylated sorbitan trioleate), sorbimacrogol oleate, synthetic amphotensides (tritons), ethylene oxide ethers of octylphenolformaldehyde condensation products, phosphatides such as lecithin, polyethoxylated fats, polyethoxylated oleotriglycerides, polyethoxylated fatty alcohols. In this context, polyethoxylated means that the relevant substances contain polyoxyethylene chains, the degree of polymerization of which is generally between 2 to 40, in particular between 10 to 20. These substances are preferably used to improve the solubility of the azelastine components.

In the case of dosage forms containing water, it is optionally possible to use additional isotonization agents. Isotonization agents which may, for example, be used are: saccharose, glucose, glycerine, sorbitol, 1,2-propylene glycol, NaCl.

The isotonization agents adjust the osmotic pressure of the formulations to the same osmotic pressure as nasal secretion. For this purpose these substances are in each case to be used in such amount that, for example, in the case of a solution, a reduction in the freezing point of 0.50° to 0.56° C. is attained in comparison to pure water. In Example 1, for instance, such substances would be used in such an amount which is iso-osmotic with 68 g of sodium chloride (0.68%).

In Example 1, it is possible to use instead of NaCl per 100 ml of solution, for example:
Glucose $1H_2O$ 3.81 g ; saccharose 6.35 g ; glycerine 2.2 g; 1,2-propylene glycol 1.617 g ; sorbitol 3.84 g (in the case of mixtures of these substances correspondingly less may optionally be used).

Moreover, it is possible to add thickening agents to the solutions to prevent the solution from flowing out of the nose too quickly and to give the solution a viscosity of about 1.5 to 3, preferably 2 mPa.s. Such thickening agents may, for example, be: cellulose derivatives (for example cellulose ether) in which the cellulose-hydroxy groups are partially etherified with lower unsaturated aliphatic alcohols and/or lower unsaturated aliphatic oxyalcohols (for example methyl cellulose, carboxymethyl cellulose, hydroxypropylmethylcellulose), gelatin, polyvinylpyrrolidone, tragacanth, ethoxose (water soluble binding and thickening agents on the basis of ethyl cellulose), alginic acid, polyvinyl alcohol, polyacrylic acid, pectin and equivalent agents. Should these substances contain acid groups, the corresponding physiologically acceptable salts may also be used.

In the event of the use of hydroxypropyl cellulose, 0.1% by weight are, for example, used for this purpose.

It is also possible to add to the formulations buffer substances such as citric acid / sodium hydrogensulphate borate buffer, phosphates (sodium hydrogenorthophosphate, disodium hydrogenphosphate), tromethamol or equivalent conventional buffers in order, for example, to adjust the formulation to a pH value of 6 to 7.5, preferably 6.5 to 7.1.

The amount of citric acid is, for example, 0.01 to 0.14, preferably 0.04 to 0.05 g, the amount of disodium hydrogenphosphate 0.1 to 0.5, preferably 0.2 to 0.3 g per 100 ml of solution. The weights given relate in each case to the anhydrous substances.

In the case of solutions and suspensions, the maximum total concentration of active agent and buffer should be less than 5%, in particular less than 2% (weight/volume).

For the nasal application a solution or suspension is preferably used which is applied as an aerosol, i.e. in the form of a fine dispersion in air or in another conventional carrier gas, for example by means of a conventional pump vaporizer.

Application as a dosage aerosol is, however, also possible. Dosage aerosols are defined as being pressure packings which contain the azelastine or its salts in the form of a solution or suspension in a so-called propellant. Propellants are pressurized liquid chlorinated, fluorinated hydrocarbons or mixtures of various chlorinated, fluorinated hydrocarbons as well as propane, butane, isobutane or mixtures of these among themselves or with chlorinated, fluorinated hydrocarbons which are gaseous at atmospheric pressure and room temperature. The pressure packing has a dosage valve which, on actuation, releases a defined amount of the solution or suspension of the medicament. The subsequent very sudden vaporization of the propellant tears the solution or suspension of azelastine into the finest droplets or minute particles which can be sprayed into the nose or which are available for inspiration into the nose. Certain plastic applicators are used to actuate the valve and to convey the sprayed suspension into the nose. Propellants that may, however, also be used are: $CO_2$, nitrous oxide and compressed air.

In the case of application as an aerosol, it is also possible to use a conventional adapter.

When suspensions are used, the maximum particle size of the solid substances (azelastine +auxiliary substances) should not exceed 30 μm.

In the case of use in the form of an insufflatable powder, the maximum particle size of the substances should not be greater than 20 μm.

What occurs is, for example, a vaporizing of solid azelastine or its salts. In this case the azelastine or its salt is, for example, mixed with inert carrier substances or drawn up onto inert carrier substances. Carrier substances which may, for example, be used are: sugars such as glucose, saccharose, lactose and fructose. Also starches or starch derivatives, oligosaccharides such as dextrins, cyclodextrins and their derivatives, polyvinylpyrrolidone, alginic acid, tylose, silicic acid, cellulose, cellulose derivatives (for example cellulose ether), sugar alcohols such as mannitol or sorbitol, calcium carbonate, calcium phosphate. The concentration of azelastine is 1 part by weight of azelastine to 50 to 200,000 parts by weight of carrier substance (0.0005 to 2% of azelastine).

DETAILED DESCRIPTION OF PREFERRED EMBODIMENTS

The invention is illustrated by the following examples.

EXAMPLE 1

Nasal spray or nasal drops or eye drops with 0.1% azelastine hydrochloride as active ingredient The following are dissolved, in the following order, into 9.00 kg of water: 10 g of azelastine hydrochloride, 5 g of edetic acid disodium salt. 2 $H_2O$, 68 g of sodium chloride, 1.25 g of alkyl-benzyldimethylammonium chloride (benzalkonium chloride), 4.38 g of citric acid, 64.8 g of sodium monohydrogen-phosphate. 12 $H_2O$ as well as 10 g of hydroxypropylmethyl cellulose.)[1]

[1] Commercially available product, for example methocel E4M premium.

The solution obtained is diluted to 10.05 kg =10 liters with water. The solution is filtered through a membrane filter of pore size 0.2 μm after careful mixing, the first 500 ml of filtrate being discarded. The filtrate has a pH value of 6.8 ±0.3. This is filled into plastic bottles which are closed with a conventional spray insert or into plastic or glass bottles which are closed with a conventional pump sprayer. In the latter case, pumps with nasal spray inserts are, for example used, which spray about 0.14 ml of solution per actuation. In this manner, 0.14 mg of azelastine hydrochloride are sprayed into the nose per actuation in the form of the solution.

If the above obtained filtrate is filled into the bottles with dropper pipettes conventionally used for nasal drops or eye drops, the solution can be dripped into the nose or eye using a dropper pipette.

EXAMPLE 2

Nasal ointment with 0.1% of azelastine hydrochloride 5 kg of polyoxyethylene stearate[2], 8 kg of cetylstearyl alcohol (Lanette 0), 20 kg of white Vaseline, 15 kg of liquid paraffin and 0.5 kg of silicon oil are melted together in a heatable vessel. 126 g of p-hydroxybenzoic acid methyl ester and 53 g of p-hydroxybenzoic acid propyl ester are dissolved in the melt (temperature of the melt 80° C.). Subsequently, a solution heated to 70° C. of 0.1 kg of azelastine hydrochloride, 140 g of p-hydroxybenzoic acid methyl ester and 60 g of p-hydroxybenzoic acid propyl ester in 51.021 kg of purified water are emulsified with the aid of a high speed stirrer and the emulsion obtained is stirred until cold and repeatedly homogenized at regular time intervals.

[2] Polyoxyethylene-40-stearate, solid, white to cream-colored mass, $D.^{25}$ ca. 1.1, F. 40°–44° C. Solidification point ca. 41° C.

The ointment is filled into tubes which have a tubular extension beyond the thread and are thus particularly suitable for applying the ointment into the nose.

EXAMPLE 3

Dosage aerosol giving off 0.5 mg of azelastine hydrochloride per stroke

About 8.0 kg of a mixture of 70 parts by weight of difluorodichloromethane and 30 parts by weight of 1,2dichlorotetrafluoroethane are cooled to about −55° C. in an appropriate cooling vessel. A mixture of 0.086 kg of precooled sorbitantrioleate and 0.8600 kg of precooled trichlorofluoromethane are dissolved with stirring into this mixture at −55° C. 0.0688 kg of micronized azelastine hydrochloride and 0.0688 kg of micronized lactose are then incorporated in portions into the solution thereby obtained with intensive stirring. The total weight of the suspension thereby obtained is made up to 9.547 kg through addition of more of the mixture of 70 parts by weight of difluorodichloromethane and 30 parts by weight of 1,2-dichlorotetrafluoroethane cooled to about −55° C.

Following closure of the cooling vessel the suspension is again cooled to about −55° C. under intensive stirring. It is then ready to be filled.

With continued stirring the suspension is filled into the conventional suitable aluminum monobloc tins. The monobloc tins are closed immediately after the suspension has been filled using conventional dosage valves which release 0.05 ml of suspension per valve actuation. Actuation of the valve thus releases 0.5 mg of azelastine hydrochloride. Presentation is effected in conjunction with a conventional applicator which permits introduction of the active substance into the nose of the patient.

EXAMPLE 4

Eye drops with 0.05% of azelastine hydrochloride 140 g of polyvinylalcohol (trade name for example: Mowiol 26–88 / Hoechst AG, Frankfurt 80) are stirred into 4 liters of cold water for injection purposes, the suspension is heated to 90° C. and left at this temperature for 45 minutes. After cooling, the solution obtained is mixed with the following solutions:

5 g of azelastine hydrochloride in 1 liter of water for injection purposes, 0.2 g of phenyl mercuric nitrate in 2 liters of water for injection purposes, 70 g of sodium chloride in 1 liter of water for injection purposes.

The mixture is adjusted to a pH value of 6.8 through addition of 0.1 N sodium hydroxide solution, mixed with a solution of 15 g of sodium dihydrogen phosphate.2 H$_2$O and 21 g of disodium hydrogen phosphate.2 H$_2$O in 1 liter of water for injection purposes and filled up to 10 liters with water for injection purposes.

Following careful mixing the solution is filtered through a membrane filter of pore size 0.2 μm with glass fiber pre-filter and filled into sterile eye drop bottles under aseptic conditions after discarding a first 500 ml of filtrate.

What is claimed is:

1. A method for the treatment of irritation or disorders of the nose and eye which comprises applying directly to nasal tissues or to the conjunctival sac of the eyes a medicament which contains a member selected from the group consisting of azelastine and its physiologically acceptable salts.

2. A method as set forth in claim 1 in which the medicament contains 0.0005 to 2% (weight/weight) of azelastine or an amount of a physiologically acceptable salt of azelastine which contains 0.0005 to 2% (weight/weight) azelastine.

3. A method as set forth in claim 2 in which the medicament contains 0.001 to 1% (weight/weight) of azelastine or an amount of a physiologically acceptable salt of azelastine which contains 0.001 to 1% (weight/weight) azelastine.

4. A method as set forth in claim 1 in which the medicament contains 0.003 to 0.5% (weight/weight) of azelastine or an amount of a physiologically acceptable salt of azelastine which contains 0.003 to 0.5% (weight/weight) azelastine.

5. A method as set forth in claim 1 in which the medicament contains a pharmaceutically usable preservative in an amount of 0.001 to 0.1%.

6. A method as set forth in claim 1 in which the medicament is a solution.

7. A method as set forth in claim 1 in which the medicament is an aqueous solution.

8. A method as set forth in claim 1 in which the medicament is a solution which contains 0.001 to 0.05% (weight/volume of solution) of sodium-2-(ethylmercurithio)-benzoate or 0.001 to 0.1% (weight/volume of solution) of alkylbenzyldimethyl ammonium chloride.

9. A method as set forth in claim 1 in which the medicament is applied by spraying.

10. A method as set forth in claim 1 in which the medicament is applied as drops.

11. A method as set forth in claim 1 in which the medicament is a powder.

12. A method for the treatment of a patient suffering from allergy-related, or vasomotor or rhino-related colds or symptoms which comprises applying directly to the patient's nasal tissues or to the conjunctival sac of the patient's eye a medicament which contains a member selected from the group consisting of azelastine and its physiologically acceptable salts.

* * * * *

UNITED STATES PATENT AND TRADEMARK OFFICE
CERTIFICATE EXTENDING PATENT TERM
UNDER 35 U.S.C. § 156

PATENT NO.      :   5,164,194

ISSUED          :   November 17, 1992

INVENTOR(S)     :   Helmut Hettche

PATENT OWNER    :   Asta Medica, AG

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 349 days from November 17, 2009, the original expiration date of the patent, subject to the payment of maintenance fees as provided by law, with all rights pertaining thereto as provided by 35 U.S.C. § 156(b).

I have caused the seal of the Patent and Trademark Office to be affixed this 27th day of February 1998.

Bruce A. Lehman
Assistant Secretary of Commerce and
Commissioner of Patents and